US006503893B2

(12) United States Patent
Bishop et al.

(10) Patent No.: US 6,503,893 B2
(45) Date of Patent: Jan. 7, 2003

(54) METHOD OF TREATING HYPERPROLIFERATIVE DISEASES USING ACTIVE VITAMIN D ANALOGUES

(75) Inventors: Charles W. Bishop, Madison, WI (US); Richard B. Mazess, Madison, WI (US)

(73) Assignee: Bone Care International, Inc., Middleton, WI (US)

(*) Notice: Subject to any disclaimer, the term of this patent is extended or adjusted under 35 U.S.C. 154(b) by 0 days.

(21) Appl. No.: 09/891,814

(22) Filed: Jun. 26, 2001

(65) Prior Publication Data

US 2002/0025950 A1 Feb. 28, 2002

Related U.S. Application Data

(60) Continuation-in-part of application No. 09/596,149, filed on Feb. 23, 1998, which is a division of application No. 08/781,910, filed on Dec. 30, 1996, now Pat. No. 5,763,429.

(51) Int. Cl.[7] ................................................ A61K 31/59
(52) U.S. Cl. ....................................... 514/167; 514/168
(58) Field of Search ................................. 514/167, 168

(56) References Cited

U.S. PATENT DOCUMENTS

| 2,383,446 A | 6/1945 | Calcott et al. |
| 3,697,559 A | 10/1972 | DeLuca et al. |
| 3,741,996 A | 6/1973 | DeLuca et al. |
| 3,907,843 A | 9/1975 | DeLuca et al. |
| 4,195,027 A | 3/1980 | DeLuca et al. |
| 4,202,829 A | 5/1980 | DeLuca et al. |
| 4,225,596 A | 9/1980 | DeLuca et al. |
| 4,234,495 A | 11/1980 | DeLuca et al. |
| 4,260,549 A | 4/1981 | DeLuca et al. |
| 4,362,710 A | 12/1982 | Watanabe |
| 4,391,802 A | 7/1983 | Suda et al. |
| 4,508,651 A | 4/1985 | Baggiolini et al. |
| 4,554,106 A | 11/1985 | DeLuca et al. |
| 4,555,634 A | 11/1985 | DeLuca et al. |
| 4,588,716 A | 5/1986 | DeLuca et al. |
| 4,661,294 A | 4/1987 | Holick et al. |
| 4,670,190 A | 6/1987 | Hesse et al. |
| 4,689,180 A | 8/1987 | DeLuca et al. |
| 4,698,328 A | 10/1987 | Neer et al. |
| 4,833,125 A | 5/1989 | Neer et al. |
| 4,866,048 A | 9/1989 | Calverley et al. |
| 5,063,221 A | 11/1991 | Nishii et al. |
| 5,104,864 A | 4/1992 | DeLuca et al. |
| 5,157,135 A | 10/1992 | Tsuji et al. |
| 5,372,996 A | 12/1994 | Labrie |
| 5,403,831 A | 4/1995 | DeLuca et al. |
| 5,448,120 A | 9/1995 | Schaule et al. |
| 5,486,636 A | 1/1996 | DeLuca et al. |
| 5,488,120 A | 1/1996 | Knutson et al. |
| 5,602,116 A | 2/1997 | Knutson et al. |
| 5,763,428 A | 6/1998 | Knutson et al. |
| 5,763,429 A | 6/1998 | Bishop et al. |
| 5,786,348 A | 7/1998 | Bishop et al. |
| 5,789,397 A | 8/1998 | Bishop et al. |
| 5,798,345 A | 8/1998 | Knutson et al. |
| 5,801,164 A | 9/1998 | Knutson et al. |
| 6,025,346 A | 2/2000 | Knutson et al. |
| 6,087,350 A | 7/2000 | Johnson et al. |
| 6,166,000 A | 12/2000 | Bishop et al. |
| 6,211,168 B1 | 4/2001 | Bishop et al. |

FOREIGN PATENT DOCUMENTS

| BE | A-877 356 | 10/1979 |
| EP | 0197514 | 10/1986 |
| EP | A-0 390 097 | 10/1990 |
| EP | 0 503 630 A1 | 3/1992 |
| EP | 0 562 497 A1 | 9/1993 |
| EP | 0 664 287 A1 | 7/1995 |
| WO | 8404527 | 11/1984 |
| WO | WO 87/00834 | 2/1987 |
| WO | WO 90/10620 | 9/1990 |
| WO | WO 92/05130 | 4/1992 |
| WO | WO 92/12165 | 7/1992 |
| WO | WO 92/21355 | 12/1992 |
| WO | WO 93/14763 | 8/1993 |
| WO | WO 94/05630 | 3/1994 |
| WO | WO 94/16711 | 8/1994 |
| WO | WO 96/40153 | 12/1996 |
| WO | WO 96/40154 | 12/1996 |
| WO | WO 97/23242 | 7/1997 |
| WO | WO 98/56387 | 12/1998 |
| WO | WO 98/56389 | 12/1998 |
| WO | WO 99/16451 | 4/1999 |
| WO | WO 99/49027 | 9/1999 |
| WO | WO 99/49870 | 10/1999 |
| WO | WO 00/03700 | 1/2000 |
| WO | WO 01/22974 | 4/2001 |
| WO | WO 01/64251 | 9/2001 |

OTHER PUBLICATIONS

L.E. Reeve et al., "Biological Activity of 1α–hydroxy Vitamin $D_2$ in the Rat" *Arch. Biochem. Biophys.* 186, Feb. 1, 1978, pp. 164–167.

Sjoden et al., "Effects of 1 $OHD_2$ on Bone Tissue" *Acta Endocrinol.* (Copenh.) 16, 4, Aug. 1984, pp. 564–568.

N. Brautbar, "Osteoporosis: Is 1,25–$(OH)_2D_3$ of Value in Treatment?" *Nephron* 44, 1986, pp. 161–166.

*Physician's Desk Reference*, Edition 43, pp. 1746–1748.

Y. Tanaka et al., *Endocrinology*, 1973, 92, pp. 417–422.

O.H. Sorenson et al., *Clin Endocrinol.*, 1977, 7, pp. 169S–175S.

V. Hoikka et al., *Acta Med. Scand.*, 1980, 207, pp. 221–224.

Brown et al., *Lancet*, 1984, 1, pp. 1091–1093.

J. Podenphant et al., *Acta Med Scand.*, 1985, 218, pp. 329–333.

(List continued on next page.)

Primary Examiner—James H Reamer
(74) Attorney, Agent, or Firm—Michael, Best & Friedrich LLP; Teresa J. Welch; Jeffrey D. Peterson

(57) ABSTRACT

Methods for the utilization of hypocalcemic vitamin D analogs to inhibit the hyperproliferation of malignant or neoplastic cells without incidence of hypercalcemia.

44 Claims, No Drawings

OTHER PUBLICATIONS

Caniggia et al., *Calif Tissue Int.,* 1986, 38, pp. 328–332.
Duda et al., *J. Clinic Invest.,* 1987, 79, pp. 1249–1253.
Sommerfeldt et al., *J. Nutr.,* 1983, 11, pp. 2595–2600.
Zerwebh et al., *J. Clin. Endocrinol. Metabol.,* 1985, 60, pp. 615–617.
Horst et al., *Anal. Biochem.,* 1981, 116, pp. 189–203.
Horst et al., *Biochem. J.,* 1982, 204, pp. 185–189.
Foldes et al., *Osteoporosis,* 1987, C. Christianson et al. (eds.) Osteopress Aps, Copenhagen, pp. 971–973.
Guidelines for the Clinical Evaluation of Drugs Used in the Treatment of Osteoporosis, HEW (FDA) 80–3094, pp. 5–6 (1979).
J.A. Kanis et al., Guidelines for Clinical Trials in Osteoporosis, A Position Paper of the European Foundation for Osteoporosis, *Osteoporosis Int.,* 1991, 1, pp. 182–188.
C. Christiansen et al., "Prevention of Early Postmenopausal Bone Loss: Controlled 2–Year Study in 315 Normal Females," *Europ J Clin Invest, 1980, 10, pp. 273–279.*
J.M. Pouilles et al., "Prevention of Early Postmenopausal Bone Loss with 1α–Hydroxy Vitamin $D_3$, A Three–Year Prospective Study," *Clin Rheumatol.,* 11, 1992, 4, pp. 492–497.
M.F. Holick et al., *Proc. Natl. Acad. Sci. USA* 68, 803–804 (1971).
G. Jones et al., *Biochemistry* 14, 1250–1256 (1975).
M.F. Holick et al., *Science* 180, 190, 191 (1973).
H.Y. Lam et al., *Science* 486, 1038–1040 (1974).
S.M. Ott, C.H. Chesnut, *Annals of Int. Med.* 1989, 110:267–274.
J.C. Gallagher et al., *Annals of Int. Med.* 1990, 113:649–655.
J. Aloia et al., *Amer. J. Med.* 84:401–08 (1988).
M. Shiraki et al., *Endocrinol. Japan* 32, 305–315 (1985).
G.F. Jensen et al., *Clin. Endocrinol.* 16, 515–524 (1982).
C. Christiansen et al., *Eur. J. Clin.* Invest. 11, 305–309 (1981).
O.H. Sorensen et al., *Clin Endocrinol.* 7, 169S–175S (1977).
H. Orimo et al., *Bone and Mineral* 3, 47–52 (1987).
G. Sjoden et al., *J. Nutr.* 114, 2043–2046 (1984).
G. Sjoden et al., *Proc. Soc. Exp. Biol. Med.* 178, 432–436 (1985).
J.C. Gallagher et al., *J. Bone Min. Res.;* 1994; 9:607–614.
E. Braunwald et al., *Harrison's Principles of Internal Medicine:* Part Eleven, "Disorders of Bone and Mineral Metabolism," Chapter 335, McGraw–Hill, New York, 1987, pp. 1860–1865.
W. Grab, *Z. Physiol. Chem.,* 243:63–89 (1936).
F.G. McDonald, *J. Biol. Chem.,* 114:IVX (1936).
A. Windaus et al., *Z. Physiol. Chem.,* 247–:185–188 (1937).
DeLuca et al., *Arch. Biochem, Biophys.,* 124:122–128 (1968).
*Merck Index,* S. Budavari (ed.), 11th ed., Merck & Co., Rahway, N.J. (1989) pp. 1579, #9930.
Barton et al., *JCS Perkin I,* 1976, 821–826.

Paaren et al., *J. Org. Chem.,* 1980, 45:3253.
S. Wientroub et al. "The Dichotomy in the Effects of 1,25 dihydroxy vitamin $D_3$ and 24, 25 dihydroxy vitamin $D_3$ on Bone Gamma–Carboxyglutamic Acid–Containing Protein in Serum and Bone in vitamin D–Deficient Rats," *Calcif, Tissue Int.* (1987) 40:166–172.
Strugnell et al., *Biochem. Pharm.* vol. 40:333–341 (1990).
Martin and DeLuca, *Am. J. Physiol.* 216:1352–1359.
P.J. Kocienski et al., *J.C.S. Perkins I,* 1290–1293 (1979).
M. Tsuji et al., *Bull. Chem. Soc. Jpn.,* vol. 63, No. 8, 2233–2238 (1990).
D.R. Crump et al., *J.C.S. Perkins Trans. I,* 2731–2733 (1973).
Chemical Abstracts, vol. 113, No. 1, Jul. 2, 1990, Columbus, Ohio, US; abstract No. 6683y, Y. Tachibana, 'Preparation of 1beta–hydroxyvitamin $D_2$ and $D_3$,' page 6688; column 2; abstract 7 JP–A–02 011 563 (Nisshin Flour Milling Co.).
Chemistry Letters, No. 8, Aug. 1985, Tokyo, JP, pp. 1131–1132, H. Nemeto et al., 'A stereoselective synthesis of 1 alpha–hydroxy–vitamin $D_3$'.
F. Sato et al., *Biochim. Biophys. Acta,* vol. 1091 (1991) pp. 188–192.
*Holick, M. F., "Noncalcemic Actions of 1,25–Dihydroxyvitamin $D_3$ and Clinical Applications", *Bone,* vol. 17, 2:107S–110S (1995).
*Knutson, et al., "Metabolism of 1α–Hydroxyvitamin $D_2$ to activated Dihydroxyvitamin $D_2$ Metabolites Decreases Endogenous 1α,25–Dihydroxyvitamin $D_3$ in Rats and Monkeys", *Endocrinology,* vol. 136, 11:4749–4753 (1995).
* Majewski, et al., "Inhibition of Tumor Cell–Induced Angiogenisis by Retinoids, 1,25–Dihydroxyvitamin $D_3$ and their Combination", *Cancer Letters,* vol. 75, 35–39 (1993).
Miller et al., "The Human Prostatic Carcinoma Cell Line LNCaP Expresses Biologically Active, Specific Receptors for 1α, 25–Dihydroxyvitamin $D_3$[1]," 52 *Cancer Res.* (1992) 515–520.
Strugnell et al., "1α,24(S)–Dihydroxyvitamin $D_2$: a biologically active product of 1α–hydroxyvitamin $D_2$ made in the human hepatoma, Hep3B," 310 *Biochem. J.* (1995) pp. 233–241.
Skowronski et al., "Actions Of Vitamin $D_3$ Analogs on Human Prostrate Cancer Cell Lines: Comparison with 1,25–Dihydroxyvitamin $D_3$," 136 *Endocrinology* (1995) 20–26.
Skowronski et al., "Vitamin D and Prostate Cancer: 1,25–Dihydroxyvitamin $D_3$ Receptors and Actions in Human Prostate Cancer Cell Lines," 132 *Endocrinology* (1993) 1952–1960.
Beer, et al., "A Phase I Trial of Pulse Calcitriol in Patients with Refractory Malignancies," *Cancer,* vol. 91, No. 12 (June 15, 2001) 2431–2439.
Beer, et al., "Weekly High–Dose Calcitriol and Docetaxel in Advanced Prostate Cancer," *Seminars in Oncology,* vol. 28, No. 4, Suppl 15 (Aug. 2001) 49–55.

METHOD OF TREATING HYPERPROLIFERATIVE DISEASES USING ACTIVE VITAMIN D ANALOGUES

CROSS-REFERENCE TO RELATED APPLICATIONS

This application is a continuation-in-part of U.S. application Ser. No. 09/596,149, filed Feb. 23, 1998, which is a divisional of U.S. application Ser. No. 08/781,910, filed Dec. 30, 1996, now U.S. Pat. No. 5,763,429 all of which are incorporated herein by reference.

STATEMENT REGARDING FEDERALLY SPONSORED RESEARCH OR DEVELOPMENT

Not Applicable

BACKGROUND OF THE INVENTION

This invention relates generally to a method of treating hyperproliferative diseases, and in particular, to the use of active forms of hypocalcemic vitamin D to inhibit the hyperproliferative cellular activity of these diseases and to promote differentiation of the cells.

Extensive research during the past two decades has established important biologic roles for vitamin D apart from its classic role in bone and mineral metabolism. Specific nuclear receptors for $1\alpha,25$-dihydroxyvitamin $D_3$, the hormonally active form of vitamin D, are present in cells from diverse organs not involved in calcium homeostasis. For example, specific, biologically active vitamin D receptors have been demonstrated in the human prostatic carcinoma cell line, LNCaP, (Miller et al., 52 Cancer Res. (1992) 515–520); Vitamin D receptors have also been described for many other neoplastic cells, e.g., carcinomas of the breast and the colon.

It has been reported that certain vitamin D compounds and analogues are potent inhibitors of malignant cell proliferation and are inducers/stimulators of cell differentiation. For example, U.S. Pat. No. 4,391,802 issued to Suda et al. discloses that $1\alpha$-hydroxyvitamin D compounds, specifically $1\alpha,25$-dihydroxyvitamin $D_3$ and $1\alpha$-hydroxyvitamin $D_3$, possess potent antileukemic activity by virtue of inducing the differentiation of malignant cells (specifically leukemia cells) to nonmalignant macrophages (monocytes), and are useful in the treatment of leukemia. Antiproliferative and differentiating actions of $1\alpha,25$-dihydroxyvitamin $D_3$ and other vitamin $D_3$ analogues have been reported with respect to cancer cell lines. More recently, an association between vitamin D receptor gene polymorphism and cancer risk has been reported, suggesting that vitamin D receptors may have a role in the development, and possible treatment, of cancer.

These previous studies have focused exclusively on vitamin $D_3$ compounds. Even though these compounds may indeed be highly effective in promoting differentiation in malignant cells in culture, their practical use in differentiation therapy as anticancer agents is severely limited because of their equally high potency as agents affecting calcium metabolism. At the levels required in vivo for effective use as, for example, antileukemic agents, these same compounds can induce markedly elevated and potentially dangerous blood calcium levels by virtue of their inherent calcemic activity. That is, the clinical use of $1\alpha,25$-dihydroxyvitamin $D_3$ and other vitamin $D_3$ analogues as anticancer agents is precluded, or severely limited, by the risk of hypercalcemia. This indicates a need for compounds with greater specific activity and selectivity of action, i.e., vitamin D compounds with antiproliferative and differentiating effects but which have less calcemic activity.

BRIEF SUMMARY OF THE INVENTION

The present invention provides a method of treating hyperproliferative disease conditions such as those characterized by hyperproliferative cell growth and/or abnormal cell differentiation. The method includes use of active vitamin D compounds to inhibit abnormal cell growth and promote cell differentiation.

The foregoing, and other advantages of the present invention, are realized in one aspect thereof in a method of inhibiting the hyperproliferative activity of neoplastic or hyperplastic cells, comprising treating the cells with an effective amount of a hypocalcemic vitamin D compound. The treating step includes inhibiting proliferation of, and inducing and enhancing differentiation in such cells.

The hypocalcemic vitamin D compounds of the present invention include vitamin D compounds having a hydrocarbon moiety substituted at the C-24 position on the sidechain of the molecule and a hydroxy group substituted in at least one of the $C_1$, $C_{24}$ or $C_{25}$ positions.

The vitamin D compound of the present invention is an active vitamin D and is suitably represented by the formula (I) described hereafter. The compounds of formula (I) suitably include $1\alpha,24$-dihydroxyvitamin $D_2$, $1\alpha,24$-dihydroxyvitamin $D_4$, $1\alpha,25$-dihydroxyvitamin $D_4$, $1\alpha,25$-dihydroxyvitamin $D_2$, $1\alpha$-hydroxyvitamin $D_2$ and $1\alpha$-hydroxyvitamin $D_4$.

Hypocalcemic vitamin D compounds are valuable for the treatment of breast and colon cancer, as well as other neoplasms such as pancreatic cancer, endometrial cancer, small cell and non-small cell cancer of the lung (including squamous, adneocarcinoma and large cell types), squamous cell cancer of the head and neck, bladder, ovarian and cervical cancers, myeloid and lymphocyltic leukemia, lymphoma, hepatic tumors, medullary thyroid carcinoma, multiple myeloma, melanoma, retinoblastoma, and sarcomas of the soft tissue and bone.

In accordance with the present invention, when effective amounts of hypocalcemic vitamin D compounds are administered to patients with cancer or neoplasms, the proliferative activity of the abnormal neoplastic cells is inhibited, reduced, or stabilized, and cell differentiation is induced, promoted or enhanced, with significantly less hypercalcemia and hypercalciuria than is observed after the same amount of an activated vitamin $D_3$ (e.g., $1\alpha$-OH $D_3$, $1\alpha,25$-$(OH)_2$ $D_3$) is administered in previously known formulations. Thus, the compound in accordance with the present invention has an improved therapeutic index relative to active forms of vitamin $D_3$ analogues.

Accordingly, another aspect of the invention is a method of treating human cancer comprising administering to a subject who has cancer an effective amount of hypocalcemic vitamin D compound which has or attains through metabolism in vivo, a vitamin D receptor (VDR) binding affinity substantially equivalent to the binding affinity of $1\alpha,25$-dihydroxyvitamin $D_3$ and a hypercalcemia risk substantially lower that that of $1\alpha,25$-dihydroxyvitamin $D_3$, to inhibit, decrease or stabilize the cellular abnormal proliferative activity of the cancer.

For treatment for malignant conditions in accordance with the present invention, the hypocalcemic vitamin D compounds can be suitably administered alone as an active ingredient, as an antiproliferative agent in a pharmaceutical composition, or co-administered with an anticancer agent.

Further, included within the scope of the present invention is the co-administration of the vitamin D of formula (I) with a cytotoxic or anticancer agent. Such agents suitably include antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophasphamide, melphalan, biochoroethylnitrosurea, hydroxyurea), platinum agents (e.g. cisplatin, carboplatin, oxaliplatin, JM-216, CI-973), anthracyclines (e.g., doxrubicin, daunorubicin), antibiolitics (e.g., mitomycin, idarubicin, adriamycin, daunomycin), topoisomerase inhibitiors (e.g., etoposide, camptothecins) or any other antineoplastic agents. (estramustine phosphate, prednimustine).

It is anticipated that the hypocalcemic vitamin D compounds used in combination with various anticancer drugs can give rise to a significantly enhanced cytotoxic effect on cancerous cells, thus providing an increased therapeutic effect. Specifically, as a significantly increased growth-inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses. Possible dose ranges of these co-administered anticancer agents are about 0.1 to 20 mg/kg/day.

Also included within the scope of the present invention is the co-administration of effective dosages of the analogue of formula (I) in conjunction with administration of hormones or other agents, e.g., estrogens, which are known to ameliorate bone diseases or disorders. For example, prostate cancer often metastasizes to bone, causing bone loss and associated pain. Such bone agents may include conjugated estrogens or their equivalents, calcitonin, bisphosphonates, calcium supplements, cobalamin, pertussis toxin and boron.

In another aspect, the invention is a pharmaceutical composition which includes an anticancer agent which is an active vitamin D compound; an agent selected from the group consisting of (i) an anticancer agent, (ii) a bone agent, and combinations thereof; and a physiologically acceptable carrier.

Other advantages and a fuller appreciation of specific adaptations, compositional variations, and physical attributes will be gained upon an examination of the following detailed description of preferred embodiments, taken in conjunction with the appended claims.

BRIEF DESCRIPTION OF THE DRAWING(S)

Not Applicable

DETAILED DESCRIPTION OF THE INVENTION

The present invention provides an effective method for the treatment of neoplasms and hyperproliferative diseases. Particularly, the present invention relates to therapeutic methods for inhibiting, reducing or stabilizing the hyperproliferative cellular activity of diseased cells, and inducing, enhancing or promoting cell differentiation in the diseased cells. The present invention provides a novel treatment of a patient suffering from a hyperproliferative disease such as prostatic cancer or prostatic hyperplasia with a hypocalcemic hydroxyvitamin D analogue. The vitamin D analogue is suitably a 1α-hydroxyvitamin D or a 24-hydroxyvitamin D compound. The hypocalcemic hydroxyvitamin D analogue represented by formula (I) as described hereinbelow is provided to the patient without causing dose-limiting hypercalcemia and hypercalciuria, i.e., unphysiologically high and deleterious blood calcium levels and urine calcium levels, respectively. These attributes are achieved through specific chemical properties of the hypocalcemic vitamin D compounds as described.

In accordance with the present invention, when effective amounts of the hypocalcemic vitamin D compounds are administered to patients with cancer or hyperplasia, the proliferative activity of the abnormal cells is inhibited, maintained, or alleviated, and cell differentiation is induced, promoted or enhanced, with significantly less hypercalcemia and hypercalciuria than is observed after the same amount of activated vitamin $D_3$ is administered in previously known formulations. Thus, the hypocalcemic vitamin D compounds of the present invention have an improved therapeutic index relative to active forms of vitamin $D_3$ analogues.

It is known that vitamin $D_3$ must be hydroxylated in the C-1 and C-25 positions before it is activated, i.e., before it will produce a biological response. A similar metabolism appears to be required to activate other forms of vitamin D, e.g., vitamin $D_2$ and vitamin $D_4$. Therefore, as used herein, the term "activated vitamin D" or "active vitamin D" is intended to refer to a vitamin D compound or analogue that has been hydroxylated in at least the C-1, C-24 or C-25 position of the molecule and either the compound itself or its metabolites in the case of a prodrug, such as 1α-hydroxyvitamin $D_2$, binds the vitamin D receptor (VDR). For example, vitamin D "prodrugs" include compounds which are hydroxylated in the C-1 position. Such compounds undergo further hydroxylation in vivo and their metabolites bind the VDR.

The term "hypocalcemic vitamin D compound" is in reference to active vitamin D analogs which demonstrate reduced calcemic activity relative to the calcemic activity of 1α,25-dihydroxyvitamin $D_3$. Such compounds include 24-hydroxyvitamin D compounds, 25-hydroxyvitamin D compounds and 1α-hydroxyvitamin D compounds. The calcemic activity of these compounds ranges from 0.001 to 0.5 that of 1α,25-dihydroxyvitamin $D_3$.

Also, as used herein, the term "lower" as a modifier for alkyl, alkenyl acyl, or cycloalkyl is meant to refer to a straight or branched, saturated or unsaturated hydrocarbon radical having 1 to 4 carbon atoms. Specific examples of such hydrocarbon radicals are methyl, ethyl, propyl, isopropyl, butyl, isobutyl, t-butyl, ethenyl, propenyl, butenyl, isobutenyl, isopropenyl, formyl, acetyl, propionyl, butyryl or cyclopropyl. The term "aromatic acyl" is meant to refer to a unsubstituted or substituted benzoyl group.

As used herein, the term "hydrocarbon moiety" refers to a lower alkyl, a lower alkenyl, a lower acyl group or a lower cycloalkyl, i.e., a straight or branched, saturated or unsaturated $C_1$–$C_4$ hydrocarbon radial.

The compound in accordance with the present invention is an active hypocalcemic vitamin D compound. Further, the active vitamin D in accordance with the present invention may have an unsaturated sidechain, e.g., there is suitably a double bond between C-22 and C-23, between C-25 and C-26 or between C-26 and C-27.

A hypocalcemic hydroxyvitamin D of the present invention has the general formula described in formula (I)

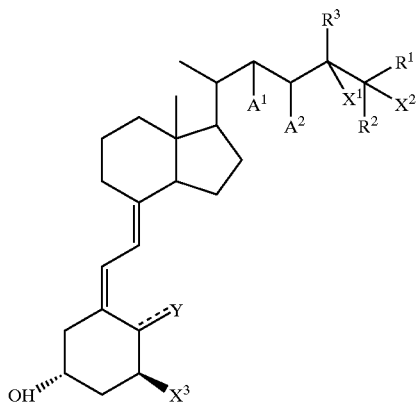

(I)

wherein $A^1$ and $A^2$ each are hydrogen or a carbon-carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that both $R^1$ and $R^2$ cannot both be an alkenyl, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, $X^2$ is hydrogen or hydroxyl, or, may be taken with $R^1$ or $R^2$, to constitute a double bond, $X^3$ is hydrogen or hydroxyl provided that at least one of $X^1$, $X^2$ and $X^3$ is hydroxyl; and Y is a methylene group if the bond to Y is a double bond or is a methyl group or hydrogen if the bond to Y is a single bond.

A 1α-hydroxyvitamin D compound of formula (I) is characterized by the general formula (II):

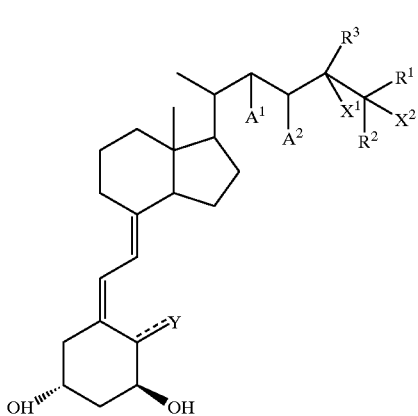

(II)

wherein $A^1$ and $A^2$ each are hydrogen or a carbon-carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that both $R^1$ and $R^2$ cannot both be an alkenyl, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, $X^2$ is hydrogen or hydroxyl, or, may be taken with $R^1$ or $R^2$, to constitute a double bond, and Y is a methylene group if the bond to Y is a double bond or is a methyl group or hydrogen if the bond to Y is a single bond.

Specific 1α-hydroxyvitamin D compounds in accordance with the present invention are characterized by the general formula (III):

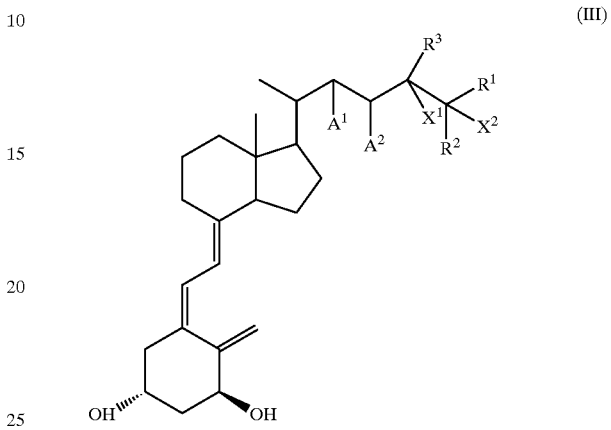

(III)

wherein $A^1$ and $A^2$ each are hydrogen or a carbon-carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that both $R^1$ and $R^2$ cannot both be an alkenyl, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, and $X^2$ is hydrogen or hydroxyl, or, may be taken with $R^1$ or $R^2$, to constitute a double bond.

The hypocalcemic vitamin D compounds of the present invention are those that have effective antiproliferative and cell differentiation activity (i.e., reversal of malignant transformation), but have a lower tendency or inability to cause the undesired side effects of hypercalcemia and/or hypercalciuria. In other words, the compounds of the present invention can be administered at dosages that allow them to act as antiproliferative agents and cell differentiation agents when exposed to malignant or other hyperproliferative cells without significantly altering calcium metabolism. This selectivity and specificity of action makes the hypocalcemic vitamin D compounds useful and preferred agents for safely inhibiting hyperproliferation and promoting malignant or hyperplastic cell differentiation. The compounds of the present invention, thus, overcome the shortcomings of the known active vitamin $D_3$ compounds described above, and can be considered preferred agents for the control and treatment of malignant diseases such breast, prostate, testicular and colon cancer, as well as other neoplasms such as pancreatic cancer, endometrial cancer, small cell and non-small cell cancer of the lung (including squamous, adneocarcinoma and large cell types), squamous cell of the head and neck, bladder, ovarian and cervical cancers, myeloid and lymphocyltic leukemia, lymphoma, hepatic tumors, medullary thyroid carcinoma, multiple myeloma, melanoma, retinoblastoma, and sarcomas of the soft tissue and bone, i.e. neoplasms that express a vitamin D receptor.

Thus, the present invention provides a method of treating malignant cells as well as other hyperproliferative cells, (i.e., inhibiting their hyperproliferative activity and/or inducing and enhancing their differentiation) with an effective amount of a hypocalcemic vitamin D compound. The effective dosage amount on a daily basis per kilogram of body weight of the patient ranges from about 0.01 μg/kg/day to about 2.0 μg/kg/day. The compounds in accordance with the present invention can be given in daily dose or episodic dose, e.g., once every 2–6 days or once a week, the dose in each day can be a single dose or divided into 2–4 subdoses which can be given, e.g., an hour apart until the total dose is given. The compounds in accordance with the present invention are administered in an amount that raises a serum vitamin D level to a supraphysiological level for a sufficient period of time to induce differentiation or regression of a tumor or neoplasm with causing hypercalcemia. The hypocalcemic properties of the compound permit such supraphysiologic levels.

The compounds of formula (I) are valuable for the treatment of cancer and neoplasms in a patient suffering therefrom. In particular, the invention is a method for treating a patient suffering from the hyperproliferative cellular effects of cancer and other neoplasms by administering to the patient a therapeutically effective amount of a compound of formula (I), which is suitably 1α,24-dihydroxyvitamin $D_2$, 1α,24-dihydroxyvitamin $D_4$, 1α,25-dihydroxyvitamin $D_2$, 1α,25-dihydroxyvitamin $D_4$, 1α-hydroxyvitamin $D_2$, and 1α-hydroxyvitamin $D_4$. Among those compounds of formula (I) that have a chiral center in the sidechain, such as at C-24, it is understood that both epimers (e.g., R and S) and the racemic mixture are within the scope of the present invention.

The compounds of formula (I) can be prepared as described, e.g., in U.S. Pat. No. 5,488,120 issued to Knutson et al., U.S. Pat. Nos. 4,554,106, 4,670,190 and 5,486,636 issued to DeLuca et al., and Strugnell et al., 310 *Biochem. J.* (1995) pp. 233–241, all of which are incorporated herein by reference.

The biopotencies of the compounds of formula(I) have been studied and compared to that of 1α,25-dihydroxyvitamin $D_3$, the active hormonal form of vitamin D and the standard against which all vitamin D compounds and analogues are measured. For example, it has been found that the vitamin D receptor (VDR) binding affinities of the compounds of formula (I), or their active metabolites, are substantially equivalent to (i.e., equal to or up to 3 times weaker than) the affinity of 1α,25-dihydroxyvitamin $D_3$. Such receptor binding affinities are indicative of potent biological activity.

At the same time, it has been found that compounds of formula (I) are significantly less toxic than their corresponding vitamin $D_3$ analogues. For example, in parent co-pending application, Ser. No. 08/265,438, the disclosure of which is incorporated herein by reference, the $LD_{50}$ for 1α-hydroxyvitamin $D_4$ was found to be 1.0 mg/kg in males and 3.0 mg/kg in females, i.e., substantially less toxic than 1α-hydroxyvitamin $D_3$ ($LD_{50}$~0.2 mg/kg). Further, in the parent U.S. Pat. No. 5,403,831, and its grandparent U.S. Pat. No. 5,104,864, both of which are incorporated herein by reference, it has been shown that 1α-hydroxyvitamin $D_2$ has the same biopotency as 1α-hydroxyvitamin $D_3$ and 1α,25-dihydroxyvitamin $D_3$ but is much less toxic. Even dosages up to 10 μg/day of 1α-hydroxyvitamin $D_2$ in women with postmenopausal osteoporosis elicited only mild hypercalciuria (U.Ca>300 mg/24 hrs), and no marked hypercalcemia (S. Ca>11.0 mg/dL) solely due to 1α-hydroxyvitamin $D_2$ was evident. Additionally, the compound did not adversely affect kidney function, as determined by creatinine clearance and BUN; nor did it increase urinary excretion of hydroxyproline, indicating the absence of any stimulatory effect on bone resorption. Administration of 1α-hydroxyvitamin $D_2$ to healthy adult males in dosages up to 8 μg/day showed no clinically significant hypercalcemia or other adverse effects.

The compounds of formula (I) are useful as active ingredients in pharmaceutical compositions having reduced side effects and low toxicity as compared with the known analogues of active forms of vitamin $D_3$.

The pharmacologically active compounds of this invention can be processed in accordance with conventional methods of pharmacy to produce medicinal agents for administration to patients, e.g., mammals including humans. For example, the hypercalcemic vitamin D compounds of the present invention can be employed in admixtures with conventional excipients, e.g., pharmaceutically acceptable carrier substances suitable for enteral (e.g., oral), parenteral or topical application which do not deleteriously react with the active compounds.

Suitable pharmaceutically acceptable carriers include but are not limited to water, salt solutions, alcohols, gum arabic, vegetable oils (e.g., almond oil, corn oil, cottonseed oil, peanut oil, olive oil, coconut oil), mineral oil, fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, flavoring and/or one or more other active compounds, for example, vitamin $D_3$ and its 1α-hydroxylated metabolites, conjugated estrogens or their equivalents, anti-estrogens, calcitonin, biphosphonates, calcium supplements, cobalamin, pertussis toxin and boron.

For parenteral application, particularly suitable are injectable, sterile solutions, preferably oily or aqueous solution, as well as suspensions, emulsions, or implants, including suppositories. Parenteral administration suitably includes subcutaneous, intramuscular, or intravenous injection, nasopharyngeal or mucosal absorption, or transdermal absorption. Where indicated, the compounds of formula (I) may be given by direct injection into the tumor, e.g., parathyroid adenoma, or by regional delivery, e.g.,by intraarterial delivery or delivery via the portal vein. Regional delivery is especially suitable for treatment of hepatic cancers. Ampoules are convenient unit dosages.

For enteral application, particularly suitable are tablets, dragees, liquids, drops, suppositories, lozenges, powders, or capsules. A syrup, elixir, or the like can be used if a sweetened vehicle is desired.

For topical application, suitable nonsprayable viscous, semi-solid or solid forms can be employed which include a carrier compatible with topical application and having a dynamic viscosity preferably greater than water, for example, mineral oil, almond oil, self-emulsifying beeswax, vegetable oil, white soft paraffin, and propylene glycol. Suitable formulations include, but are not limited to, creams, ointments, lotions, solutions, suspensions, emulsions, powders, liniments, salves, aerosols, transdermal patches, etc., which are, if desired, sterilized or mixed with auxiliary agents, e.g., preservatives, stabilizers, demulsifiers, wetting agents, etc. A cream preparation in accordance with the present invention suitably includes, for example, mixture of water, almond oil, mineral oil and self-emulsifying beeswax; an ointment preparation suitably includes, for example, almond oil and white soft paraffin; and a lotion preparation suitably includes, for example, dry propylene glycol.

Topical preparations of the compound in accordance with the present invention useful for the treatment of skin disorders may also include epithelialization-inducing agents such as retinoids (e.g., vitamin A), chromanols such as vitamin E, β-agonists such as isoproterenol or cyclic adenosine monophosphate (cAMP), anti-inflammatory agents such as corticosteroids (e.g., hydrocortisone or its acetate, or dexamethasone) and keratoplastic agents such as coal tar or anthralin. Effective amounts of such agents are, for example, vitamin A about 0.003 to about 0.3% by weight of the composition; vitamin E about 0.1 to about 10%; isoproterenol about 0.1 to about 2%; cAMP about 0.1 to about 1%; hydrocortisone about 0.25 to about 5%; coal tar about 0.1 to about 20%; and anthralin about 0.05 to about 2%.

For rectal administration, the compound is formed into a pharmaceutical composition containing a suppository base such as cacao oil or other triglycerides. To prolong storage life, the composition advantageously includes an antioxidant such as ascorbic acid, butylated hydroxyanisole or hydroquinone.

For treatment of calcium metabolic disorders, oral administration of the pharmaceutical compositions of the present invention is preferred. Generally, the compound of this invention is dispensed by unit dosage form comprising about 0.5 µg to about 25 µg in a pharmaceutically acceptable carrier per unit dosage. The dosage of the compound according to this invention generally is about 0.01 to about 1.0 µg/kg/day, preferably about 0.04 to about 0.3 g/kg/day. Oral dosing for the treatment of cancers and neoplasms and other hyperproliferative diseases generally is about 10 µg to 200 µg/day.

For topical treatment of skin disorders, the dosage of the compound of the present invention in a topical composition generally is about 0.01 µg to about 50 µg per gram of composition. For treatment of cancers, the dosage of the hypocalcemic vitamin D compound in a locally applied composition generally is about 0.01 µg to 100 µg per gram composition.

Oral administration of the pharmaceutical compositions of the present invention is preferred. The dosage of the compounds for the treatment of cancer or neoplasms according to this invention generally is about 0.01 to about 2.0 µg/kg/day, preferably about 0.01 to about 1.0 µg/kg/day. As noted above, dosing of the hypocalcemic vitamin D compounds in accordance with the present invention can be done on an episodic basis, in which higher does can be used, generally about 20 µg to about 200 µg given once every 2–7 days. Generally, the compounds of this invention are dispensed by unit dosage form in a pharmaceutically acceptable carrier.

Those of ordinary skill in the art will readily optimize effective doses and coadministration regimens as determined by good medical practice and the clinical condition of the individual patient. Regardless of the manner of administration, it will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, body weight, general state of health, on diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

Further, included within the scope of the present invention is a method of co-administration of hypercalcemic vitamin D compounds with an anticancer or antineoplastic agent. Such agents may suitably include antimetabolites (e.g., 5-fluorouracil, methotrexate, fludarabine), antimicrotubule agents (e.g., vincristine, vinblastine, taxanes such as paclitaxel, docetaxel), an alkylating agent (e.g., cyclophasphamide, melphalan, biochoroethylnitrosurea, hydroxyurea), platinum agents (e.g. cisplatin, carboplatin, oxaliplatin, JM-216, CI-973), anthracyclines (e.g., doxrubicin, daunorubicin), antibiolitics (e.g., mitomycin, idarubicin, adriamycin, daunomycin), topoisomerase inhibitiors (e.g., etoposide, camptothecins) or any other antineoplastic agents. (estramustine phosphate, prednimustine). It is anticipated that hypercalcemic vitamin D compounds used in combination with various anticancer drugs can give rise to a significantly enhanced cytotoxic effect on cancerous cells, thus providing an increased therapeutic effect. Specifically, as a significantly increased growth-inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses. Possible dose ranges of these co-administered anticancer agents are about 0.1 to 20 mg/kg/day.

The term "co-administration" is meant to refer to any administration route in which two or more agents are administered to a patient or subject. For example, the agents may be administered together, or before or after each other. The agents may be administered by different routes, e.g., one agent may be administered intravenously while the second agent is administered intramuscularly, intravenously or orally. The agents may be administered simultaneously or sequentially, as long as they are given in a manner sufficient to allow both agents to achieve effective concentrations in the body. The agents also may be in an admixture, as, for example, in a single tablet. In sequential administration, one agent may directly follow administration of the other or the agents may be give episodically, i.e., one can be given at one time followed by the other at a later time, typically within a week. An example of a suitable co-administration regimen is where a hypocalcemic vitamin D compound is administered from 0.5 to 7 days prior to administration of a cytotoxic agent.

Also included within the scope of the present invention is the co-administration of effective dosages of hypercalcemic vitamin D compounds in conjunction with administration of hormones or other agents, e.g., estrogens, which are known to ameliorate bone diseases or disorders. For example, prostate cancer often metastasizes to bone, causing bone loss and associated pain. Such bone agents may include conjugated estrogens or their equivalents, calcitonin, bisphosphonates, calcium supplements, cobalamin, pertussis toxin and boron. Possible dose ranges for these co-administered bone agents are provided in Table 1.

TABLE 1

Possible Oral Dose Ranges for Various Bone Agents
Co-Administered With 1α-Hydroxyvitamin D of Formula (I)

| Agent | Broad | Preferred | Most Preferred |
|---|---|---|---|
| Conjugated Estrogens or Equivalent (mg/day) | 0.3–5.0 | 0.4–2.4 | 0.6–1.2 |
| Sodium Fluoride (mg/day) | 5–150 | 30–75 | 40–60 |
| Calcitonin (IU/day) | 5–800 | 25–500 | 50–200 |
| Bisphosphonates (mg/day) | 0.5–20 | 1–15 | 5–10 |
| Calcium Supplements (mg/day) | 250–2500 | 500–1500 | 750–1000 |
| Cobalamin (μg/day) | 5–200 | 20–100 | 30–50 |
| Pertussis Toxin (mg/day) | 0.1–2000 | 10–500 | 100–1000 |
| Boron (mg/day) | 0.10–3000 | 1–250 | 2–100 |

Antiestrogens, such as Tamoxifen ™, are also known bone agents and may be suitably used in conjunction with the 1α-hydroxyvitamin D compounds of the present invention.

The present invention is further explained by the following examples which should not be construed by way of limiting the scope of the present invention.

VDR BINDING ANALYSES

EXAMPLE 1

1α,24-Dihydroxyvitamin $D_2$ [1α,24-$(OH)_2D_2$]

The affinity of 1α,24-$(OH)_2D_2$ for the mammalian vitamin D receptor (VDR) was assessed using a commercially available kit of bovine thymus VDR and standard 1,25-$(OH)_2D_3$ solutions from Incstar (Stillwater, Minn.). The half-maximal binding of chemically synthesized 1α,24-$(OH)_2D_2$ was approximately 150 pg/ml whereas that of 1α,25-$(OH)_2D_3$ was 80 pg/ml. Thus, the 1α,24-$(OH)_2D_2$ had a very similar affinity for bovine thymus VDR as did 1α,25-$(OH)_2D_3$, indicating that 1α,24-$(OH)_2D_2$ has potent biological activity.

EXAMPLE 2

1α,24-Dihydroxy Vitamin $D_4$ [1α,24-$(OH)_2D_4$]

The VDR affinity binding of 1α,24-$(OH)_2D_4$ was investigated. The 1α,24-$(OH)_2D_4$ was incubated with vitamin D receptor and radiolabeled tracer 1α,25-$(OH)_2D_3$. After incubation, the amount of radioactivity bound to the receptor was determined and compared with the amount bound after co-incubation of unlabeled and labeled 1α,25-$(OH)_2D_3$. It was found that 50 pg/tube of 1α,24-$(OH)_2D_4$ was equivalent to approximately 20 pg 1α,25-$(OH)_2D_3$.

These results show that 1α,24-$(OH)_2D_4$ binds slightly less tightly to the vitamin D receptor than does 1α,25-$(OH)_2D_3$. Such data mean that 1α,24-$(OH)_2D_4$ has high affinity for the VDR and significant biological activity, similar to that of 1α,25-$(OH)_2D_3$. These data are consistent with gene expression studies done (described below) with 1α,24-$(OH)_2D_4$ which demonstrate that 1α,24-$(OH)_2D_4$ is only slightly less active than is 1α,25-$(OH)_2D_3$.

These results are surprising and unexpected in view of the prior art. They are contrary to the normative wisdom in the vitamin D art regarding the very low degree of biological activity of vitamin $D_4$ compounds.

EXAMPLE 3

1α,24-Dihydroxyvitamin $D_2$ [1α,24-$(OH)_2D_2$]

VDR binding of vitamin D compounds by prostate cells is demonstrated using the techniques of Skowronski et al., 136 *Endocrinology* (1995) 20–26, which is incorporated herein by reference. Prostate-derived cell lines are cultured to near confluence, washed and harvested by scraping. Cells are washed by centrifugation, and the cell pellet resuspended in a buffered salt solution containing protease inhibitors. The cells are disrupted by sonication while cooling on ice. The supernatant obtained from centrifuging the disrupted cells at 207,000×g for 35 min at 4EC is assayed for binding. 200 TL of soluble extract, (1-2 mg protein/ml supernatant) is incubated with a 1 nM $^3$H-1α,25-$(OH)_2D_3$ and increasing concentrations of 1α,24-$(OH)_2$-$D_2$ (0.01–100 nM) for 16–20 hr at 4EC. Bound and free hormones are separated with hydroxylapatite using standard procedures. Specific binding is calculated by subtracting nonspecific binding obtained in the presence of a 250-fold excess of nonradioactive 1α,25-$(OH)_2D_3$ from the total binding measured. The results demonstrate that 1α,24-$(OH)_2D_2$ has strong affinity for prostate VDR, indicating that 1α,24-$(OH)_2D_2$ has potent biological activity in respect of prostate cells.

EXAMPLE 4

1α,24-Dihydroxy Vitamin $D_4$ [1α,24-$(OH)_2D_4$]

The procedure of Example 3 is repeated using the active vitamin D analogue 1α,24-$(OH)_2D_4$, and the specific binding is determined. The results demonstrate that 1α,24-$(OH)_2D_4$ has strong affinity for prostate VDR, indicating that 1α,24-$(OH)_2D_4$ has potent biological activity in respect of prostate cells.

EXAMPLE 5

1α,25-Dihydroxyvitamin $D_4$ [1α,25-$(OH)_2D_4$]

The procedure of Example 3 is repeated using the active vitamin D analogue 1α,25-$(OH)_2D_4$, and the specific binding is determined. The results demonstrate that 1α,25-$(OH)_2D_4$ has strong affinity for prostate VDR, indicating that 1α,25-$(OH)_2D_4$ has potent biological activity in respect of prostate cells.

GENE EXPRESSION

EXAMPLE 6

1α,24-Dihydroxy Vitamin $D_4$ [1α,24-$(OH)_2D_4$]

Using the plasmids p(CT4)$^4$TKGH, a vitamin D receptor (VDR)-expressing plasmid, and pSG5-hVDR1/3, a plasmid containing a Growth Hormone (GH) gene, under the control of a vitamin D-responsive element (VDRE), experiments were conducted to explore the ability of 1α,24-$(OH)_2D_4$ to induce vitamin D-dependent growth hormone acting as a reporter gene compared to that of 1α,25-$(OH)_2D_3$. Cells in culture were transfected with these two plasmids. One plasmid contained the gene for Growth Hormone (GH) under the control of the vitamin D responsive element (VDRE) and the other plasmid contained the structural gene for the vitamin D receptor (VDR). These transfected cultures were incubated with 1α,24-$(OH)_2D_4$ or 1α,25-$(OH)_2D_3$, and the production of growth hormone was measured. Table 2 below shows the results of this assay:

TABLE 2

Induction of Growth Hormone by Vitamin D Compounds

| Compound | Concentration Used (M) | Growth Hormone Induction (ng/ml) |
|---|---|---|
| 1,25-(OH)$_2$D$_3$ | 1 × 10$^{-10}$ | 39 |
| 1,25-(OH)$_2$D$_3$ | 5 × 10$^{-10}$ | 248 |
| 1,24-(OH)$_2$D$_4$ | 5 × 10$^{-10}$ | 165 |
| 1,24-(OH)$_2$D$_4$ | 1 × 10$^{-9}$ | 628 |
| 1,24-(OH)$_2$D$_4$ | 5 × 10$^{-9}$ | 1098 |

These data show that the ability of 1α,24-(OH)$_2$D$_4$ to stimulate vitamin D-dependent growth hormone is nearly equivalent to that of 1α,25-(OH)$_2$D$_3$. Such results are truly surprising and would not have been expected by following the teachings of the prior art.

EXAMPLE 7

1α,24(S)-Dihydroxyvitamin D$_2$ and 1α,24(R)-Dihydroxy-vitamin D$_2$ [1α,24(S)-(OH)$_2$D$_2$ and 1α,24(R)-(OH)$_2$D$_2$]

The gene expression study described in Example 6 was conducted to compare the biological activity in vitro of chemically synthesized 1α,24(S)-(OH)$_2$D$_2$ and 1α,24(R)-(OH)$_2$D$_2$, with 1α,25-(OH)$_2$D$_3$ and 25-OH-D$_3$. The vitamin D-dependent transcriptional activation model system was used in which plasmids pSG5-hVDR1/3 and p(CT4)$^4$TKGH were co-transfected into Green monkey kidney, COS-1 cells.

Transfected cells were incubated with vitamin D metabolites and growth hormone production was measured. As shown in Table 3, both 1α,24(S)-(OH)$_2$D$_2$ and its epimer, 1α,24(R)-(OH)$_2$D$_2$, had significantly more activity in this system than 25-OH-D$_3$, with 1α,24(S)-(OH)$_2$D$_2$ having nearly the same activity as 1α,25-(OH)$_2$D$_3$.

TABLE 3

Vitamin D-Inducible Growth Hormone Production In Transfected COS-1 Cells

| Inducer | Molar Concentration | Total GH Production* (ng/ml) | Vitamin DCInducible Growth Hormone Production Net vitamin DCinducible GH-production (ng/ml) |
|---|---|---|---|
| Ethanol | | 44 | 0 |
| 25-OH-D$_3$ | 1 × 10$^{-7}$ | 245 | 201 |
| | 1 × 10$^{-6}$ | 1100 | 1056 |
| | 1 × 10$^{-5}$ | 775 | 731 |
| 1α,25-(OH)$_2$D$_3$ | 1 × 10$^{-10}$ | 74 | 30 |
| | 1 × 10$^{-9}$ | 925 | 881 |
| | 1 × 10$^{-8}$ | 1475 | 1441 |
| 1α,24(S)-(OH)$_2$D$_2$ | 5 × 10$^{-10}$ | 425 | 381 |
| | 5 × 10$^{-9}$ | 1350 | 1306 |
| | 5 × 10$^{-8}$ | 1182 | 1138 |
| 1α,24(R)-(OH)$_2$D$_2$ | 1 × 10$^{-9}$ | 80 | 36 |
| | 1 × 10$^{-8}$ | 1100 | 1056 |
| | 1 × 10$^{-7}$ | 1300 | 1256 |

*Averages of duplicate determinations

INHIBITION OF CELL PROLIFERATION

EXAMPLE 8

1α,24-Dihydroxyvitamin D$_2$ [1α,24-(OH)$_2$D$_2$]

Inhibition of cell proliferation is demonstrated using the techniques of Skowronski et al., 132 *Endocrinology* (1993) 1952–1960 and 136 *Endocrinology* (1995) 20–26, both of which are incorporated herein by reference. The cell lines, LNCaP and PC-3, which are derived from human prostate adenocarcinoma, are seeded in six-well tissue culture plates at a density of about 50,000 cells/plate. After the cells have attached and stabilized, about 2–3 days, the medium is replenished with medium containing vehicle or the active vitamin D analogue 1α,24-(OH)$_2$D$_2$, at concentrations from 10$^{-11}$ M to 10$^{-7}$ M. Medium containing test analogue or vehicle is replaced every three days. After 6–7 days, the medium is removed, the cells are rinsed, precipitated with cold 5% trichloroacetic acid, and washed with cold ethanol. The cells are solubilized with 0.2 N sodium hydroxide, and the amount of DNA determined by standard procedures. The results show that cultures incubated with 1α,24-(OH)$_2$D$_2$ in accordance with the present invention have significantly fewer cells than the control cultures.

EXAMPLE 9

1α,24-Dihydroxy Vitamin D$_4$ [1α,24-(OH)$_2$D$_4$]

The procedure of Example 8 is repeated using the active vitamin D analogue 1α,24-(OH)$_2$D$_4$, and the cell number is determined. Cultures incubated with 1α,24-(OH)$_2$D$_4$ have significantly fewer cells than the control cultures.

EXAMPLE 10

1α,25-Dihydroxyvitamin D$_4$ [1α,25-(OH)$_2$D$_4$]

The procedure of Example 8 is repeated using the active vitamin D analogue 1α,25-(OH)$_2$D$_4$, and the cell number is determined. Cultures incubated with 1α,25-(OH)$_2$D$_4$ have significantly fewer cells than the control cultures.

STIMULATION OF CELL DIFFERENTIATION

EXAMPLE 11

1α,24-Dihydroxyvitamin D$_2$ [1α,24-(OH)$_2$D$_2$]

Using the techniques of Skowronski et al., 132 *Endocrinology* (1993) 1952–1960 and 136 *Endocrinology* (1995) 20–26, both of which are incorporated herein by reference, cells of the cell line, LNCaP, which is derived from a human metastatic prostate adenocarcinoma and known to express PSA, are seeded in six-well tissue culture plates at a density of about 50,000 cells/plate. After the cells have attached and stabilized, about 2–3 days, the medium is replenished with medium containing vehicle or the active vitamin D analogue, 1α,24-(OH)$_2$D$_2$, at concentrations from 10$^{-11}$ M to 10$^{-7}$ M. After 6–7 days, the medium is removed and stored at −20EC for prostate specific antigen (PSA) analysis.

The cells from parallel cultures are rinsed, precipitated, and the amount of DNA determined by standard procedures. PSA is measured by standard known methods. Cultures incubated with 1α,24-(OH)$_2$D$_2$ have significantly more PSA than control cultures when expressed as mass of PSA/cell.

EXAMPLE 12

1α,24-Dihydroxyvitamin D$_4$ [1α,24-(OH)$_2$D$_4$]

The procedure of Example 12 is repeated except the active vitamin D analogue is 1α,24-(OH)$_2$D$_4$. The PSA is measured and cultures incubated with 1α,24-(OH)$_2$D$_4$ have significantly more PSA than control cultures when expressed as mass of PSA/cell.

EXAMPLE 13

1α,25-Dihydroxy Vitamin D$_4$ [1α,24-(OH)$_2$D$_4$]

The procedure of Example 12 is repeated except the active vitamin D analogue is 1α,25-(OH)$_2$D$_4$. The PSA is measured and cultures incubated with $1\alpha,25\text{-}(OH)_2D_4$ have significantly more PSA than control cultures when expressed as mass of PSA/cell.

CLINICAL STUDIES

EXAMPLE 14

General Treatment of Cancers

Patients with a known vitamin D receptor positive tumor (e.g., adenocarcinoma of the prostate, breast, lung, colon or pancreas, or transitional cell carcinoma of the bladder, or melanoma) participate in an open-label study of a hypocalcemic vitamin D compound in accordance with the present invention. Patients are placed on a reduced calcium diet prior to treatment, to help minimize intestinal absorption and allow ever higher doses of the hypocalcemic vitamin D. This reduced calcium diet may be continued for the duration of treatment, and for one week after the last dose of the $1\alpha,24(S)$-dihydroxyvitamin $D_2$. The diet ideally restricts daily calcium intake to 400–500 mg. Patients also discontinue use of any vitamin D supplements or vitamin D replacement therapies. Each patient is also asked to drink 4–6 cups of fluid more than usual intake to assure adequate oral hydration.

Each subject is monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The dosing regimen is typically on a daily dose basis of 10 µg or 20 µg per day to about 100 µg/day for 24 months. Alternatively, a non-daily dosing regimen can be used, e.g., 40 µg given every other day, 100 µg given once a week. The route of administration can vary from oral to intravenous to regional delivery (e.g., arterial infusion, via the portal vein). Oral is, of course, the easiest and most cost effective route. Regional delivery permits high dosing and generally avoids any production of hypercalcemia. Although, in the case of the compound of the present invention, the compound is substantially hypocalcemic.

After 18 months of treatment, CAT, scans, X-rays and bone scans used for evaluating the progress of metastatic disease or partial remission in many patients treated at the lower dosage, and stable disease and partial or complete remission in many patients treated at the higher dosage.

EXAMPLE 15

Treatment of Prostate Cancer with $1\alpha,24$-Dihydroxy Vitamin $D_2$ [$1\alpha,24\text{-}(OH)_2D_2$]

Patients with advanced androgen-independent prostate cancer participate in an open-labeled study of $1\alpha,24\text{-}(OH)_2D_2$. Qualified patients are at least 40 years old, exhibit histologic evidence of adenocarcinoma of the prostate, and present with progressive disease which had previously responded to hormonal intervention(s). On admission to the study, patients begin a course of therapy with oral $1\alpha,24\text{-}(OH)_2D_2$ lasting 26 weeks, while discontinuing any previous use of calcium supplements, vitamin D supplements, and vitamin D hormone replacement therapies. During treatment, the patients are monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The study is conducted in two phases. During the first phase, the maximal tolerated dosage (MTD) of daily oral $1\alpha,24\text{-}(OH)_2D_2$ is determined by administering progressively higher dosages to successive groups of patients. All doses are administered in the morning before breakfast. The first group of patients is treated with 25.0 µg of $1\alpha,24\text{-}(OH)_2D_2$. Subsequent groups of patients are treated with 50.0, 75.0 and 100.0 µg/day. Dosing is continued uninterrupted for the duration of the study unless serum calcium exceeds 11.6 mg/dL, or other toxicity of grade 3 or 4 is observed, in which case dosing is held in abeyance until resolution of the observed toxic effect(s) and then resumed at a level which has been decreased by 10.0 µg.

Results from the first phase of the study show that the MTD for $1\alpha,24\text{-}(OH)_2D_2$ is above 20.0 µg/day, a level which is 10- to 40-fold higher than can be achieved with $1\alpha,25\text{-}(OH)_2D_3$. Analysis of blood samples collected at regular intervals from the participating patients reveal that the levels of circulating $1\alpha,24\text{-}(OH)_2D_2$ increase proportionately with the dosage administered, rising to maximum levels well above 100 pg/mL at the highest dosages, and that circulating levels of $1\alpha,25\text{-}(OH)_2D_3$ are suppressed, often to undetectable levels. Serum and urine calcium are elevated in a dose responsive manner. Patients treated with the MTD of $1\alpha,24\text{-}(OH)_2D_2$ for at least six months report that bone pain associated with metastatic disease is significantly diminished.

During the second phase, patients are treated with $1\alpha,24\text{-}(OH)_2D_2$ for 24 months at 0.5 and 1.0 times the MTD. After one and two years of treatment, CAT scans, X-rays and bone scans used for evaluating the progression of metastatic disease show stable disease or partial remission in many patients treated at the lower dosage, and stable disease and partial or complete remission in many patients treated at the higher dosage.

EXAMPLE 16

Treatment of Prostate Cancer with $1\alpha$-Hydroxy Vitamin $D_2$ [$1\alpha\text{-}OH\text{-}D_2$]

The study of Example 14 is repeated for the active vitamin D compound, $1\alpha\text{-}OH\text{-}D_2$. The results of the phase one study indicate that patients treated with the MTD of $1\alpha\text{-}OH\text{-}D_2$ for at least six months report that bone pain associated with metastatic disease is significantly diminished. The results of the phase two study indicate that after two years, CAT scans, X-rays and bone scans used for evaluating the progression of metastatic disease show stable disease or partial remission in many patients treated at the lower dosage, and stable disease and partial or complete remission in many patients treated at the higher dosage.

EXAMPLE 17

Treatment of Melanoma

The method of Example 14 is used to treat patients with metastatic malignant melanoma of, e.g., the jaw. After 18 months of treatment, the progress of the metastatic disease shows stable disease or partial remission.

EXAMPLE 18

Treatment of Retinoblastoma

The method of Example 14 is used is used to treat patients with metastatic retinoblastoma. After 18 months of treatment, the progress of the metastatic disease shows stable disease or partial remission.

EXAMPLE 19

Treatment of Liver Cancer

The method of Example 14 is used to treat patients with hepatoma. The regional delivery of the compound in accordance with the present invention, i.e., via arterial infusion, is used. After 18 months of treatment, the progress of the metastatic disease shows stable disease or partial remission.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation lawfully accorded the appended claims.

What is claimed is:

1. A method of inhibiting hyperproliferation of malignant or neoplastic cells, comprising treating the cells with an antiproliferative amount of a hypocalcemic hydroxyvitamin D compound having a hydrocarbon moiety at the $C_{24}$ position, the cells expressing a vitamin D receptor.

2. A method in accordance with claim 1, wherein the cells are cancers of the breast, colon, lung, neck and head, pancreas, endometrium, bladder, cervix, testes, ovaries, and liver, squamous cell carcinoma, myeloid and lymphocytic leukemia, lymphoma, medullary thyroid carcinoma, melanoma, multiple myeloma, retinoblastoma or sarcomas of the soft tissues and bone.

3. A method in accordance with claim 1, wherein the hypocalcemic vitamin D is a compound represented by formula (I)

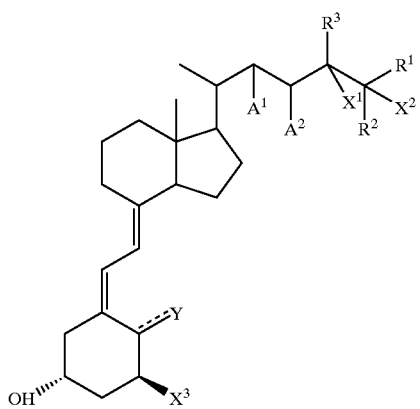

(I)

wherein $A^1$ and $A^2$ each are hydrogen or a carbon-carbon bond, thus forming a double bond between C-22 and C-23; $R^1$ and $R^2$ are identical or different and are hydrogen, hydroxyl, lower alky, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, or, taken with $R^3$, constitutes a bond when $R^3$ is an alkenyl group, and $X^2$ is hydrogen or hydroxyl, or, taken with $R^1$ or $R^2$, constitutes a double bond, and $X^3$ is hydrogen or hydroxyl provided that at least one of $X^1$, $X^2$ and $X^3$ is hydroxyl; and Y is a methylene group if the bond to Y is a double bond or is a methyl group or hydrogen if the bond to Y is a single bond.

4. A method in accordance with claim 1 wherein the hypocalcemic vitamin D compound is a compound of formula II

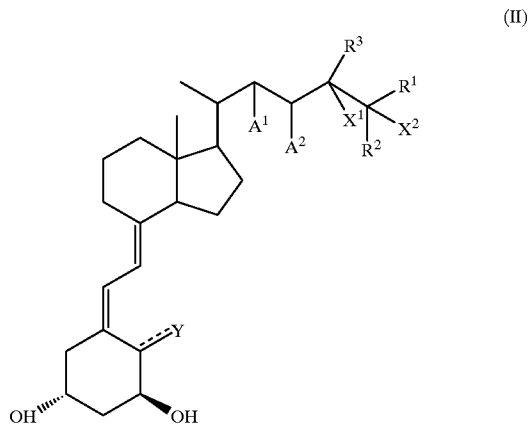

(II)

wherein $A^1$ and $A^2$ each are hydrogen or a carbon-carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, or, taken with $R^3$, constitutes a bond when $R^3$ is an alkenyl group, and $X^2$ is hydrogen or hydroxyl, or, taken with $R^1$ or $R^2$, constitutes a double bond, and Y is a methylene group if the bond to Y is a double bond or is a methyl group or hydrogen if the bond to Y is a single bond.

5. A method in accordance with claim 1, wherein the hypocalcemic vitamin D compound is a compound of formula III:

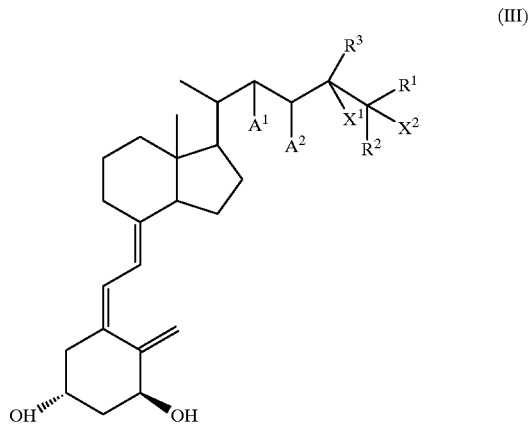

(III)

wherein $A^1$ and $A^2$ each are hydrogen or a carbon-carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, or, taken with $R^3$, constitutes a bond when $R^3$ is an alkenyl group, and $X^2$ is hydrogen or hydroxyl, or, taken with $R^1$ or $R^2$, constitutes a double bond.

6. A method of inhibiting the hyperproliferative activity of malignant or neoplastic cells, comprising administering to a patient suffering therefrom, an anitproliferarive amount of a hypocalcemic hydroxyvitamin D compound.

7. A method in accordance with claim 6, wherein the hypocalcemic vitamin D compound is administered in a daily regimen or an episodic regimen.

8. A method in accordance with claim 7, wherein the episodic regimen is a dose once every 2 to 7 days.

9. A method in accordance with claim 7, wherein the hypocalcemic vitamin D compound is administered daily at a dose of about 10 to 100 μg/day.

10. A method in accordance with claim 6, wherein the hypocalcemic vitamin D compound is administered orally, is administered intravenously, is directly injected to a cancer site or is regionally delivered to a cancer site.

11. A method in accordance with claim 10, wherein the hypocalcemic vitamin D compound is administered orally.

12. A method in accordance with claim 6, wherein the hypocalcemic vitamin D compound is co-administered with a cytotoxic agent.

13. A method in accordance with claim 12, wherein the cytotoxic agent is an antimetabolite, and antimicrotubule agent, an alkyating agent, a platinum agent, an anthracycline, a topoisomase inhibitor, or an antibiotic.

14. A method in accordance with claim 13, wherein the antimetabolite is 5-fluoro-uracil, methotrexate or fludarabine.

15. A method in accordance with claim 13, wherein the antimicrotubule agent is vincristine, vinblastine or a taxane.

16. A method in accordance with claim 14, wherein the taxane is paclitaxel or docetaxel.

17. A method in accordance with claim 12, wherein the alkylating agent is cyclophasphamide, melphalan, biochoroethylnitrosurea or hydroxyurea.

18. A method in accordance with claim 12, wherein the platinum agent is cisplatin, carboplatin, oxaliplatin, JM-216 or CI-973.

19. A method in accordance with claim 12, wherein the anthracycline is doxrubicin or daunorubicin.

20. A method in accordance with claim 12, wherein the antibiotic is mitomycin, idarubicin, adriamycin or daunomycin.

21. A method in accordance with claim 12, wherein the topoisomerase inhibitior is etoposide or camptothecins.

22. A method in accordance with claim 12, wherein the cytotoxic agent is estramustine phosphate or prednimustine.

23. A method in accordance with claim 11, wherein an antiproliferative effective amount of the cytotoxic agent is lower than the antiproliferative effective amount of the cytotoxic agent when administered alone.

24. The method of claim 5, wherein the compound of formula (III) is 1α,24-dihydroxyvitamin $D_2$, 1α,24-dihydroxyvitamin $D_4$, 1α,25-dihydroxyvitamin $D_2$, 1α,25-dihydroxyvitamin $D_4$, 1α-hydroxyvitamin $D_2$ or 1α-hydroxyvitamin $D_4$.

25. A method of treating a human to alleviate the pathological effects of breast cancer, colon cancer, testicular cancer, pancreatic cancer, endometrial cancer, small cell and non-small cell cancer of the lung (including squamous, adneocarcinoma and large cell types), squamous cell of the head and neck, bladder, ovarian and cervical cancers, myeloid and lymphocyltic leukemia, lymphoma, hepatic tumors, medullary thyroid carcinoma, multiple myeloma, melanoma, retinoblastoma or sarcomas of the soft tissue and bone, comprising administering to the human an therapeutic amount of a hypocalcemic hydroxyvitamin D compound.

26. A method of claim 25, wherein said hypocalcemic vitamin D is a 1α-hydroxyvitamin D compound represented by formula (III)

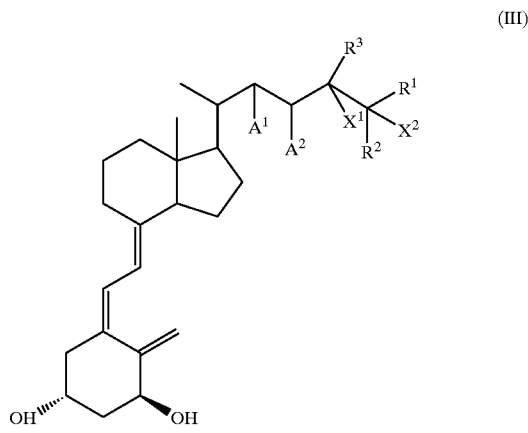

(III)

wherein $A^1$ and $A^2$ each are hydrogen or a carbon-carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, or, taken with $R^3$, constitutes a bond when $R^3$ is an alkenyl group, and $X^2$ is hydrogen or hydroxyl, or, taken with $R^1$ or $R^2$, costitutes a double bond.

27. The method of claim 26, wherein said therapeutic amount is 0.01 μg/kg/day to 2.0 μg/kg/day.

28. The method of claim 26, wherein the compound of formula (III) is 1α,24-dihydroxyvitamin $D_2$, 1α,24-dihydroxyvitamin $D_4$, 1α,25-dihydroxyvitamin $D_2$, 1α,25-dihydroxyvitamin $D_4$, 1α-hydroxyvitamin $D_2$ or 1α-hydroxyvitamin $D_4$.

29. A method of enhancing the antiproliferative effect of a cytotoxic agent in a patient with a disease in need of treatment by a cytotoxic agent, comprising administering to the patient a therapeutic amount of hypocalcemic vitamin D compound and the cytotoxic agent.

30. A method in accordance with claim 29, wherein the hypocalcemic vitamin D compound is administered from 0.5 to 7 days prior to administration of the cytotoxic agent.

31. A method in accordance with claim 29, wherein the hypocalcemic vitamin D compound is administered 2 to 4 days prior to administration of the cytotoxic agent.

32. A method of claim 29, wherein said hypocalcemic vitamin D is a 1α-hydroxyvitamin D compound represented by formula (III)

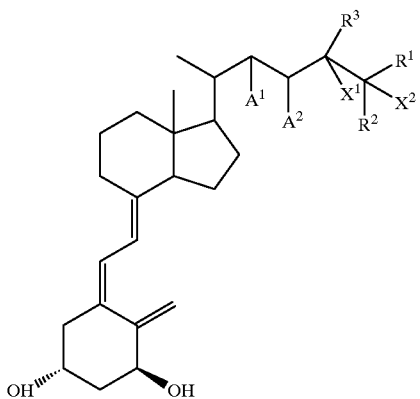

(III)

wherein $A^1$ and $A^2$ each are hydrogen or a carbon-carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, or, taken with $R^3$, constitutes a bond when $R^3$ is an alkenyl group, and $X^2$ is hydrogen or hydroxyl, or, taken with $R^1$ or $R^2$, constitutes a double bond.

33. The method of claim 32, wherein said therapeutic amount of the vitamin D compound is 0.01 μg/kg/day to 2.0 μg/kg/day.

34. The method of claim 32, wherein the compound of formula (III) is 1α,24-dihydroxyvitamin $D_2$, 1α,24-dihydroxyvitamin $D_4$, 1α25-dihydroxyvitamin $D_2$, 1α,25-dihydroxyvitamin $D_4$, 1α-hydroxyvitamin $D_2$ or 1α-hydroxyvitamin $D_4$.

35. A method in accordance with claim 32, wherein the cytotoxic agent is an antimetabolite, and antimicrotubule agent, an alkyating agent, a platinum agent, an anthracycline, a topoisomase inhibitor, or an antibiotic.

36. A method of inducing differentiation in malignant or neoplastic cells, comprising treating to the cells with a prodifferentiative amount of a hypocalcemic vitamin D compound.

37. A method of treating in a subject tumor or neoplasm that expresses a vitamin D receptor, comprising administering to the subject an effective amount of hypocalcemic vitamin D compound sufficient to raise a blood level of vitamin D to a sufficiently supraphysiological level for a sufficient period of time to inhibit growth of the tumor or neoplasm without causing hypercalcemia in the subject.

38. A method in accordance with claim 7, wherein the hypocalcemic vitamin D compound is administered episodically at a dose of about 10 μg to 200 μg/dose.

39. A method in accordance with claim 8, wherein the hypocalcemic vitamin D compound is administered at a dose of about 10 μg to 200 μg/dose.

40. A method in accordance with claim 25, wherein the pathological effects are due to hepatic tumors.

41. A method in accordance with claim 25, wherein the pathological effects are due to retinoblastoma.

42. A method in accordance with claim 25, wherein the therapeutic amount is administered episodically.

43. A method in accordance with claim 42, wherein the therapeutic amount is 10 μg to 200 μg/dose.

44. A method in accordance with claim 29, wherein the therapeutic amount of the hypocalcemic vitamin D compound is 10 μg to 200 μg/dose.

* * * * *

UNITED STATES PATENT AND TRADEMARK OFFICE
CERTIFICATE OF CORRECTION

PATENT NO. : 6,503,893 B2
DATED : June 2, 2004
INVENTOR(S) : Charles W. Bishop and Richard B. Mazess It is certified that error appears in the above-identified patent and that said Letters Patent is hereby corrected as shown below:

Column 5,
Line 30, "$X^2$is" should read -- $X^2$ is- --.

Column 9,
Line 35, "0.3 g/kg/day" should read -- 0.3 $\mu$g/kg/day --.

Column 11,
TABLE 1, Line 16, "10-500" should read -- 10-1500 --.

Column 16,
Lines 25 and 44, "sixmonths" should read -- six months --.
Line 64, "is used" should be deleted.

Column 22,
Line 1, "1α25-dihydroxyvitamin" should read -- 1α,25-dihydroxyvitamin --.

Signed and Sealed this

Twenty-fifth Day of October, 2005

JON W. DUDAS
*Director of the United States Patent and Trademark Office*